(12) United States Patent
Romanczuk et al.

(10) Patent No.: US 6,541,245 B1
(45) Date of Patent: Apr. 1, 2003

(54) ADENOVIRAL HELPER VECTORS

(75) Inventors: Helen Romanczuk, Framingham; Samuel C. Wadsworth, Shrewsbury; Patricia Berthelette, Uxbridge, all of MA (US)

(73) Assignee: Genzyme Corporation, Cambridge, MA (US)

(*) Notice: Subject to any disclaimer, the term of this patent is extended or adjusted under 35 U.S.C. 154(b) by 0 days.

(21) Appl. No.: 09/718,034

(22) Filed: Nov. 21, 2000

Related U.S. Application Data

(63) Continuation of application No. PCT/US00/25131, filed on Sep. 14, 2000, and a continuation of application No. 09/662,596, filed on Sep. 14, 2000, now abandoned, which is a continuation-in-part of application No. 60/155,758, filed on Sep. 23, 1999.

(51) Int. Cl.⁷ ..................... C12N 15/73; C12N 15/79; C12N 15/66; C12N 15/865; C12N 15/06

(52) U.S. Cl. ..................... 435/320.1; 435/235.1; 435/325.1; 435/440; 435/455; 435/91.1; 435/91.4; 435/91.41; 424/190.1; 424/93.6; 424/93.21; 424/199.1; 514/172.3

(58) Field of Search ................ 435/235.1, 325, 435/320.1, 440, 455, 91.1, 91.4, 91.41; 514/172.3, 44; 424/93.6, 93.21, 190.1, 199.1

(56) References Cited

U.S. PATENT DOCUMENTS 5,882,877 A   3/1999   Gregory et al. .......... 435/320.1

FOREIGN PATENT DOCUMENTS

| WO | WO 97/45550 | | 4/1997 |
| WO | WO 98/13510 A1 | * | 4/1998 |
| WO | WO 00/11155 | | 2/2000 |

OTHER PUBLICATIONS

Thorpe et al/ Pro. nat. Acad. Sci. USA 1998, vol. 95, pp. 5505–5510.*
Gao, et al. J. Virol. 1996, vol. 70, pp. 8934–8943.*
Schmid et al. "Biparture Structure and Functional Independence of Adenovirus Type 5 Packaging Elements", Journal of Virology, May 1999, pp. 3375–3384.
Schmid et al. "Cellular Components Interact with Adenovirus Type 5 Minimal DNA Packaging Domains" Journal of Virology, Aug. 1998, pp. 6339–6347.
Stillman, Bruce "The Replication of Adenovirus DNA with Purified Proteins" Cell, vol. 35, No. 7–9, Nov., 1983.
Hearing et al. "Identification of a Repeated Sequence Element Required for Efficient Encapsidation of the Adenovirus Type 5 Chromosome" Journal of Virology, Aug. 1987, pp. 2555–2558.
Hoess et al. "P1 site–specific recombination: nucleotide sequence of the recombining sites" Proc. Natl. Acad. Scie USA, 1982, Jun.; 79(11):3398–402.
Hardy et al. "Construction of adenovirus vectors through Cre–lox recombination" J. Virol. 1997, Mar.; 71(3):1842–9.
Shaikh et al. "The Cre recombinase cleaves the lox site in trans", J. Biol. Chem. 1997, Feb. 28; 272(9):5695–702 (Abstract).
Hamilton et al. "Site–specific recombination by the bacteriophage P1 lox–Cre system. Cre–mediated synapsis of two lox sites" J. Mol. Biol. 1984, Sep. 15; 178(2):481–6.

\* cited by examiner

*Primary Examiner*—Ali R. Salimi
*Assistant Examiner*—Bao Qun Li
(74) *Attorney, Agent, or Firm*—Jennifer L. Dupre

(57) ABSTRACT

The present invention is directed to improved helper vectors and cell lines for the production of pseudoadenoviral (PAV) vectors containing substantially reduced levels of contaminating helper vector. The invention provides for helper vectors for the production of substantially helper vector-free PAV stocks comprising phag C31 recombinase recognition sequences which, depending upon their arrangement within the helper vector, can prevent helper vector packaging. The invention also provides for improved cell lines for the production of substantially helper vector-free PAV stocks comprising a stably introduced novel circular PAV genome into the cell.

7 Claims, 9 Drawing Sheets

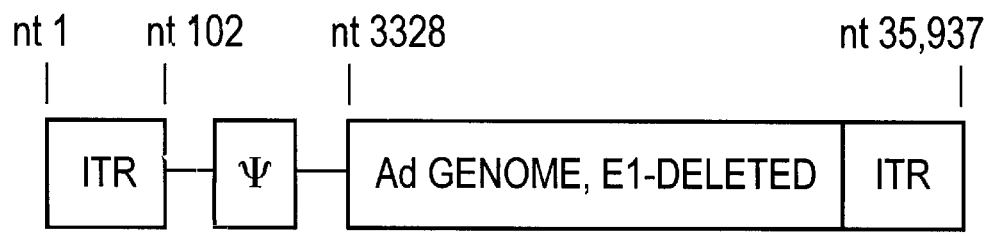
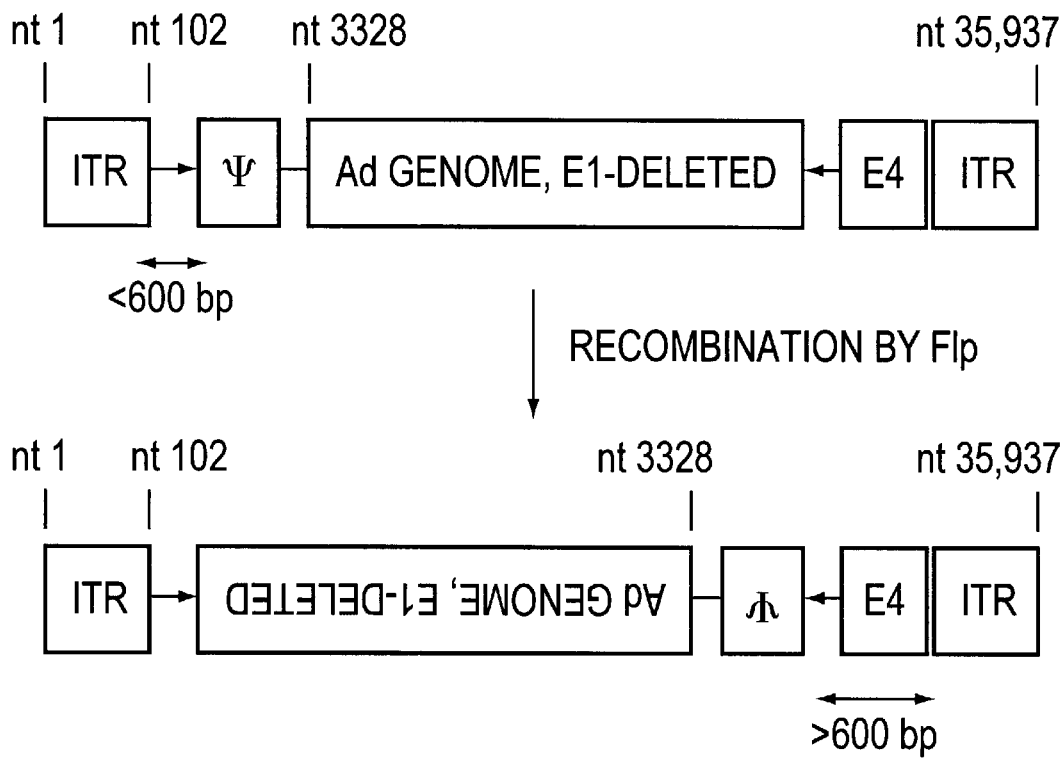

wt RECOMBINANT Ad GENOME pAdFRT/del HELPER VECTOR

RECOMBINATION BY Flp

SEQUENCE LISTING

<160> NUMBER OF SEQ ID NOS: 14

<210> SEQ ID NO 1
<211> LENGTH: 34
<212> TYPE: DNA
<213> ORGANISM: yeast

<400> SEQUENCE: 1
gaagttccta ttctctagaa agtataggaa cttc                                    34

<210> SEQ ID NO 2
<211> LENGTH: 34
<212> TYPE: DNA
<213> ORGANISM: Bacteriophage P1

<400> SEQUENCE: 2
ataacttcgt ataatgtatg ctatacgaag ttat                                    34

<210> SEQ ID NO 3
<211> LENGTH: 7
<212> TYPE: DNA
<213> ORGANISM: bacteria

<400> SEQUENCE: 3 cggaccg                                                                   7

<210> SEQ ID NO 4
<211> LENGTH: 7
<212> TYPE: DNA
<213> ORGANISM: bacteria

<400> SEQUENCE: 4 cggtccg                                                                   7

<210> SEQ ID NO 5
<211> LENGTH: 34
<212> TYPE: DNA
<213> ORGANISM: bacteriophage C31

<400> SEQUENCE: 5
gtgccagggc gtgcccttgg gctccccggg cgcg                                    34

<210> SEQ ID NO 6
<211> LENGTH: 39
<212> TYPE: DNA
<213> ORGANISM: bacteriophage C31

<400> SEQUENCE: 6
ccccaactgg ggtaacctt gagttctctc agttggggg                                39

<210> SEQ ID NO 7
<211> LENGTH: 31
<212> TYPE: DNA
<213> ORGANISM: bacteriophage C31

<400> SEQUENCE: 7
accgctcgag atgacacaag gggttgtgac c                                       31

<210> SEQ ID NO 8
<211> LENGTH: 31
<212> TYPE: DNA
<213> ORGANISM: bacteriophage C31

```
<400> SEQUENCE: 8
gtcgactagt ctacgccgct acgtcttccg t                                     31

<210> SEQ ID NO 9
<211> LENGTH: 100
<212> TYPE: DNA
<213> ORGANISM: bacteriophage C31

<400> SEQUENCE: 9
ctagtcccca actggggtaa cctttgagtt ctctcagttg ggggcgcgta atatttgtct      60
agggccgcgg ggactttgac cgtttacgtg gagactcgcg                           100

<210> SEQ ID NO 10
<211> LENGTH: 89
<212> TYPE: DNA
<213> ORGANISM: bacteriophage C31

<400> SEQUENCE: 10
ctccacgtaa acggtcaaag tccccgcggc cctagacaaa tattacgcgc ccccaactga      60
gagaactcaa aggttacccc agttgggga                                        89

<210> SEQ ID NO 11
<211> LENGTH: 93
<212> TYPE: DNA
<213> ORGANISM: bacteriophage C31

<400> SEQUENCE: 11
taatatttgt ctagggccgc ggggactttg accgtttacg tggagactgc tagcgtgcca      60
gggcgtgccc ttgggctccc cgggcgcgac gcg                                   93

<210> SEQ ID NO 12
<211> LENGTH: 100
<212> TYPE: DNA
<213> ORGANISM: bacteriophage C31

<400> SEQUENCE: 12
cgcgtcgcgc ccggggagcc caagggcacg ccctggcacg ctagcagtct ccacgtaaac      60
ggtcaaagtc cccgcggccc tagacaaata ttacgcgagt                           100

<210> SEQ ID NO 13
<211> LENGTH: 18
<212> TYPE: DNA
<213> ORGANISM: bacteriophage C31

<400> SEQUENCE: 13
gtgacgtagt agtgtggc                                                    18

<210> SEQ ID NO 14
<211> LENGTH: 19
<212> TYPE: DNA
<213> ORGANISM: bacteriophage C31

<400> SEQUENCE: 14
acactacgac ctacactgg                                                   19
```

ADENOVIRAL HELPER VECTORS

The present application is a continuation of International patent application PCT/US00/25131, filed on Sep. 14, 2000, and a patent application Ser. No. 09/662,596, filed on Sep. 14, 2000, now abandoned, and both are continuation-in-part of the application Ser. No. 60/155,758, filed Sep. 23, 1999.

FIELD OF INVENTION

The present invention is directed to improved adenoviral helper vectors that facilitate the production of pseudoadenoviral vectors (PAV), wherein the helper vectors themselves cannot be packaged into viral particles efficiently. While the helper vectors of the present invention are engineered, such that during PAV manufacture they are packaging defective, they may provide replication functions and viral structural proteins in trans for PAV. The helper vectors of the present invention comprise recombinase protein recognition sequences, wherein said recognition sequences are inserted into regions of the helper vector genome to allow for separation of the replication and packaging elements of the helper vector. Action by the cognate recombinase on such recombinase protein recognition sequences create an inversion or deletion of the genome upon recombination, thereby positioning the packaging elements such that the helper genome cannot be packaged. The invention is also directed to improved cell lines for the production of PAV which facilitate PAV stock production. The improved producer cell lines are stably transfected with a novel PAV. The combination of the novel helper vectors of the present invention, the novel PAVs and the improved cell lines facilitate PAV stock production and make the invention adaptable to large scale commercial production of PAV stocks.

BACKGROUND OF INVENTION

Adenoviral vectors for use to deliver transgenes to cells for applications such as in vivo gene therapy and in vitro study and/or production of the products of transgenes, commonly are derived from adenoviruses by deletion of the early region 1 (E1) genes (Berkner, K. L., Curr. Top. Micro. Immunol. 158:39–66, 1992). Deletion of E1 genes renders such adenoviral vectors replication defective and significantly reduces expression of the remaining viral genes present within the vector. However, it is believed that the presence of the remaining viral genes in adenoviral vectors can be deleterious to the transfected cell for one or more of the following reasons: (1) stimulation of a cellular immune response directed against expressed viral proteins, (2) cytotoxicity of expressed viral proteins, and (3) replication of the vector genome leading to cell death.

One solution to this problem has been the creation of pseudoadenoviral vectors (PAVs), which are adenoviral vectors derived from the genome of an adenovirus that contain minimal cis-acting nucleotide sequences required for the replication and packaging of the vector genome and which can contain one or more transgenes (See, U.S. Pat. No. 5,882,877 which covers pseudoadenoviral vectors (PAV) and methods for producing PAV, incorporated herein by reference). Such PAVs, which can accommodate up to about 36 kb of foreign nucleic acid, are advantageous because the carrying capacity of the vector is optimized, while the potential for host immune responses to the vector or the generation of replication-competent viruses is reduced. PAV vectors contain the 5' inverted terminal repeat (ITR) and the 3' ITR nucleotide sequences that contain the origin of replication, and the cis-acting nucleotide sequence required for packaging of the PAV genome, and can accommodate one or more transgenes with appropriate regulatory elements, e.g. promoters, enhancers, etc.

Adenoviral vectors, such as PAVs, have been designed to take advantage of the desirable features of adenovirus which render it a suitable vehicle for delivery of nucleic acids to recipient cells. Adenovirus is a non-enveloped, nuclear DNA virus with a genome of about 36 kb, which has been well-characterized through studies in classical genetics and molecular biology (Hurwitz, M. S., *Adenoviruses Virology*, 3rd edition, Fields et al., eds., Raven Press, New York, 1996; Hitt, M. M. et al., *Adenovirus Vectors, The Development of Human Gene Therapy*, Friedman, T. ed., Cold Spring Harbor Laboratory Press, New York, 1999). The viral genes are classified into early (designated E1–E4) and late (designated L1–L5) transcriptional units, referring to the generation of two temporal classes of viral proteins. The demarcation of these events is viral DNA replication. The human adenoviruses are divided into numerous serotypes (approximately 47, numbered accordingly and classified into 6 groups: A, B, C, D, E and F), based upon properties including hemaglutination of red blood cells, oncogenicity, DNA and protein amino acid compositions and homologies, and antigenic relationships.

Recombinant adenoviral vectors have several advantages for use as gene delivery vehicles, including tropism for both dividing and non-dividing cells, minimal pathogenic potential, ability to replicate to high titer for preparation of vector stocks, and the potential to carry large inserts (Berkner, K. L., Curr. Top. Micro. Immunol. 158:39–66, 1992; Jolly, D., Cancer Gene Therapy 1:51–64, 1994).

PAVs have been designed to take advantage of the desirable features of adenovirus which render it a suitable vehicle for gene delivery. While adenoviral vectors can generally carry inserts of up to 8 kb in size by the deletion of regions which are dispensable for viral growth, maximal carrying capacity can be achieved with the use of adenoviral vectors containing deletions of most viral coding sequences, including PAVs. See U.S. Pat. No. 5,882,877 of Gregory et al.; Kochanek et al., Proc. Natl. Acad. Sci. USA 93:5731–5736, 1996; Parks et al., Proc. Natl. Acad. Sci. USA 93:13565–13570, 1996; Lieber et al., J. Virol. 70:8944–8960, 1996; Fisher et al., Virology 217:11–22, 1996; U.S. Pat. No. 5,670,488; PCT Publication No. WO 96/33280, published Oct. 24, 1996; PCT Publication No. WO 96/40955, published Dec. 19, 1996; PCT Publication No. WO 97/25446, published Jul. 19, 1997; PCT Publication No. WO 95/29993, published Nov. 9, 1995; PCT Publication No. WO 97/00326, published Jan. 3, 1997; Morral et al., Hum. Gene Ther. 10:2709–2716, 1998.

Since PAVs are deleted for most of the adenovirus genome, production of PAVs requires the furnishing of adenovirus proteins in trans which facilitate the replication and packaging of a PAV genome into viral vector particles. Most commonly, such proteins are provided by infecting a producer cell with a helper adenovirus containing the genes encoding such proteins. However, such helper viruses are potential sources of contamination of a PAV stock during purification and can pose potential problems when administering the PAV to an individual if the contaminating helper adenovirus can replicate and be packaged into viral particles.

It is advantageous to increase the purity of a PAV stock by reducing or eliminating any production of helper vectors which can contaminate preparation. Several strategies to reduce the production of helper vectors in the preparation of a PAV stock are disclosed in U.S. Pat. No. 5,882,877, issued Mar. 16, 1999; U.S. Pat. No. 5,670,488, issued Sep. 23, 1997 and International Patent Application No. PCT/US99/03483, incorporated herein by reference. For example, the helper vector may contain mutations in the packaging sequence of its genome to prevent its packaging, an oversized adenoviral genome which cannot be packaged due to size constraints of the virion, or a packaging signal region with binding sequences that prevent access by packaging proteins to this signal which thereby prevents production of the helper virus.

Other strategies include the design of a helper virus with a packaging signal flanked by the excision target site of a recombinase, such as the Cre-Lox system (Parks et al., *Proc. Natl. Acad. Sci. USA* 93:13565–13570, 1996; Hardy et al.,*J. Virol.* 71:1842–1849, 1997, incorporated herein by reference). Such helper vectors reduce the yield of wild-type levels.

Another hurdle for PAV manufacturing, aside from the problems with obtaining helper vector-free stocks, is that the production process is initiated by DNA transfections of the PAV genome and the helper genome into a suitable cell line, e.g., 293 cells. After cytopathic effects are observed in the culture indicating a successful infection, which may take up to from 2 to 6 days, the culture is harvested and is passaged onto a new culture of cells. This process is repeated for several additional passages, up to 7 times more, to obtain a modest cell lysate containing the PAV vector and any contaminating helper vector. See Parks et al., 1996, *Proc. Natl. Acad. Sci. USA* 93:13565–13570; Kochanek et al., 1996, *Proc. Natl. Acad. Sci. USA* 93:5731–5736. This lengthy process is not optimal for commercial scale manufacturing. Additionally, this process facilitates recombination and rearrangement events resulting in the propagation of PAV genomes with unwanted alterations.

Therefore, there is a need for improved helper vectors which promote the production of substantially helper vector-free PAV stocks and there is a need for improved cell lines which simplify the PAV stock production process while being adaptable to large scale commercial production.

SUMMARY OF THE INVENTION

In general, it is the object of the present invention to provide improved helper vectors and cell lines for the production of pseudoadenoviral (PAV) and other adenoviral vectors containing substantially reduced levels of contaminating helper vector. The invention provides for helper vectors for the production of substantially helper vector-free PAV stocks comprising recombinase recognition sequences (e.g. Cre/Lox, Flp/FRT system, and phage [φ] C31) which, depending upon their arrangement within the helper vector, can prevent helper vector packaging. In a particularly preferred embodiment of the invention, the recombinase recognition sequences employed are those from phage C31. Phage C31 recombinase appears to be able to promote recombination/excision in a manner similar to Cre/Lox or Flp, but will not perform the reverse reaction to re-insert the excised piece. In theory, this recombinase should eliminate the generation of mutations and re-insertions that make the helper resistant to recombinase activity.

The invention also provides for improved cell lines for the production of substantially helper vector-free PAV stocks comprising a stably introduced novel circular PAV genome into the cell.

The term "PAV" is used generally to refer to recombinant adenoviral vectors from which a significant portion of the adenoviral genome has been deleted. In addition to fully deleted adenoviral vectors, such as those described in WO94/12649 [Gregory et al.]; WO99/64577 [Morsy et al.]; WO96/33280 [Zhang et al.]; WO 98/54345 [Zhang et al.]; WO95/29993 [Nabel et al.]; Balague et al., *Blood,* 95:820–828 (2000); and Fisher et al., *Virology,* 217:11–22 (1996); Vincent et al., *Nature Genetics,* 5:130–134 (1993); Sandig et al., *PNAS USA* 97:1002–1007(2000); Morsey et al., *Molecular Medicine Today: Reviews,* 1999:18–24 (1999), other partially deleted adenoviral vectors may be used in the methods of the present invention in place of PAVs. These include those described in U.S. Pat. No. 6,063,622 [Chamberlain et al.], U.S. Pat. No. 6,093,567 [Graham et al.], U.S. Pat. No. 6,093,567 [Gregory et al.], WO99/57296 [Wadsworth et al.] and WO00/12740 [Amalfitano et al.], the disclosures of all of these publications are hereby incorporated herein by reference.

During the production of recombinant adenoviral stock, the functions of the deleted portion of the adenoviral genome may be supplied in trans, usually via co-infection with a replication incompetent helper virus, or by culturing the virus in a stock of transfected packaging cells. The methods and materials of the present invention are useful for methods of producing recombinant adenoviral stocks with improved efficiency and safety characteristics.

In one embodiment, the helper vector provides adenovirus (Ad) functions in trans and comprises an adenoviral genome containing recombinase recognition sequences placed in an inverted orientation relative to each other such that the action of the recombinase on the cognate recombinase recognition sequences inverts the central portion of the helper vector genome and displaces the packaging elements from their close proximity to both or either of the 5' and 3' ITR. This displacement results in the packaging elements being moved to a distance of approximately 3,000 nucleotides from the ITR. Since the distance from the ITR required for the proper functioning of the adenovirus (e.g. Ad5) packaging motif is approximately 600 nucleotides from the ITR, such a recombination event compromises packaging of the helper vector while leaving intact the genes encoding replication functions and structural proteins necessary for the packaging of the PAV.

In another embodiment, the recombinase recognition sequences in the helper vector are placed in the same orientation and at opposite ends of the helper genome. Action of the recombinase on the cognate recombinase recognition sequences leads to formation of a circular helper genome molecule and a separate short linear DNA that contains the left and right ITRs, i.e. the ITRs are excised entirely out of the genome. The excision of the ITRs results in a helper genome which cannot be packaged because the packaging sequences are no longer adjacent to an ITR as required. Alternative replication origins, such as those from SV40 and EBV, may be incorporated into the helper genome to allow for continued replication of the circular helper genome. Additionally, the requisite nucleotides encoding required replication proteins to drive replication of the helper genome, such as SV40 large T antigen or EBNA which bind to the origin and initiate replication, may also be provided.

In a further embodiment, the helper vector comprises a packaging signal region flanked by recombinase (e.g. FRT, or phage [φ] C31 target sequences) such that binding of a recombinase at the recombinase nucleotide binding sequences results in excision of the packaging signal region from the helper vector. The genome of the helper vector may further comprise stuffer sequences which may improve excision of the packaging elements therefrom.

Another object of the invention is to provide improved cell lines for the production of PAV stocks. Such improved cell lines comprise a circular PAV genome comprising a bacterial plasmid genome (e.g. pBR322), or an origin of replication and drug resistance sequences derived from a bacterial plasmid genome (e.g. pBR322) to allow propagation of the PAV in bacteria, and eukaryotic and/or viral replication origin sequences (e.g. EBV sequences) to allow replication of the PAV genome within the mammalian producer cell line. PAV production is initiated by infection of the cell line with a suitable helper vector, such as those described above comprising recombination recognition sequences for the prevention of helper vector production. The helper vector provides, in trans, replication and packaging functions required for the production of PAV stocks. Since the circular PAV genome has its ITR sequences embedded (i.e. not at a terminus), its replication and packaging efficiencies are low. However, it is known that at a low frequency, excision of at least one ITR occurs which allows for efficient replication and packaging at its occurrence. Graham, 1984, *EMBO J.* 3:2917–2922; Matani et al, 1995, *Proc. Natl. Acad. Sci. USA* 92:3854–3858; Hardy et al., 1997, *J. Virol.* 71:1842–1849; Fisher et al., 1996, *Virol.* 217:11–22). Alternatively, the circular PAV genome is constructed such that there is a head-to-tail duplication of the ITR adjacent to the packaging sequence as would exist when Ad DNA is being replicated as a linear concatenate. See, e.g., Graham, 1984, *EMBO J.* 3:2917–2922; Fisher et al., 1996, *Virol.* 217:11–22. Excision of the ITR from this configuration is more efficient than from a single ITR. The circular PAV genome may comprise restriction endonuclease sites at positions just beyond the ITRs which, when excised by a restriction endonuclease, make the ITRs accessible and allow for efficient replication and packaging of the PAV. The helper vector may provide nucleotide sequences encoding for the appropriate restriction endonuclease (e.g. RsrII, I-Ceu I, I-Ppo I; available from New England Biolabs, Beverly, Mass.).

BRIEF DESCRIPTION OF THE DRAWINGS

FIG. 1 shows a schematic diagram of an adenovirus helper vector whose genome, including a packaging signal, is flanked by two recombinase recognition sites placed in an inverted orientation relative to each other.

Figure 2A:
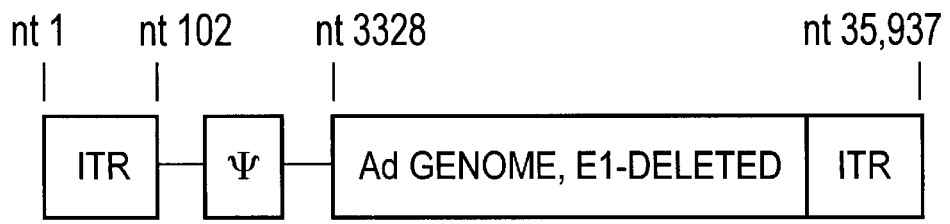
FIG. 2 shows a schematic diagram of an adenovirus helper vector whose genome contains two recombinase recognition sites placed in the same orientation and at opposite ends of the helper genome.

(Panel A) For PCR analysis, subconfluent 293 or 293/Flpe6 cells were infected with helper virus containing an FRT flanked packaging sequence. Viral DNA was extracted 3 days later and PCR amplified with primers flanking the FRT sites. Expected sizes are 421 bp (helper 1) and 462 bp (helper 2) for "unflipped" and 261 bp for "flipped" products. (Panel B) Subconfluent 293 or 293/Flpe6 cells were infected with helper virus in a 6-well dish. Cells were harvested 3 days later and one tenth of the lysate was passaged onto subconfluent 293 or 293/Flpe6 cells. Cells were harvested 3 days later and the lysated subjected to titer analysis. Infected cells were monitored by expression of enhanced green fluorescent protein (EGFP)(Panel C).

Figure 5:
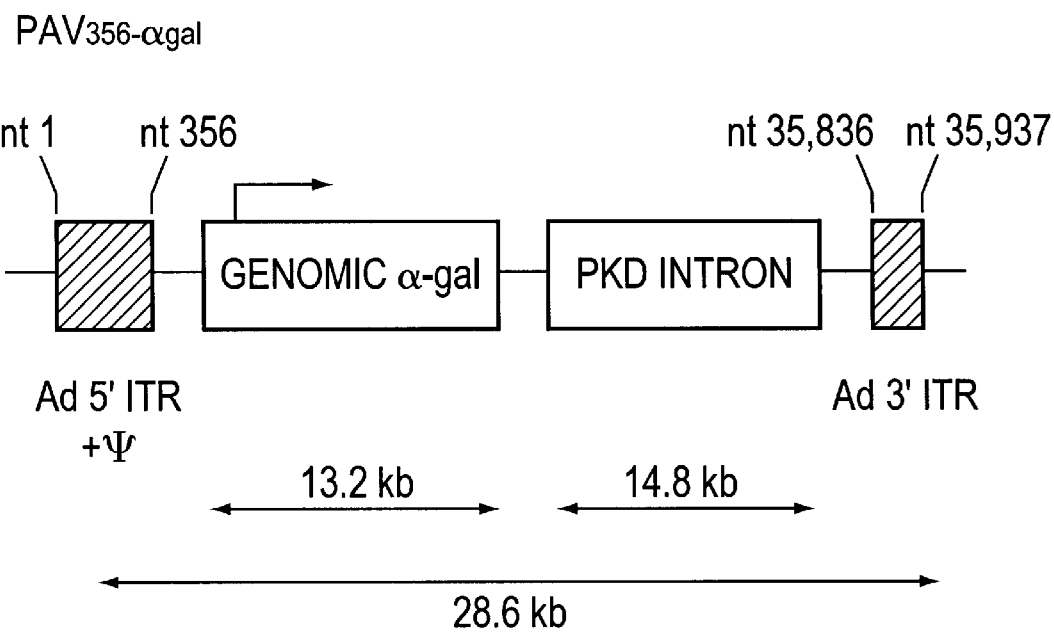

FIG. 5 shows a schematic diagram of a PAV vector comprising the 5' ITR and packaging sequences of Ad2 (nucleic acids 1–356) separated by a multiple cloning site into which is inserted a nucleic acid encoding αgal.

Figure 6:
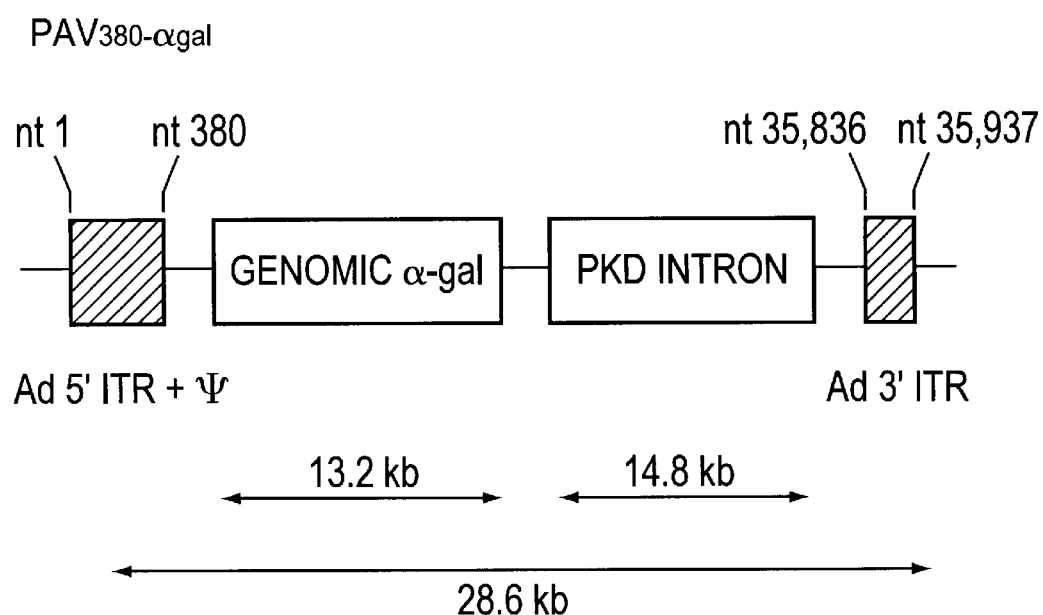

FIG. 6 shows a schematic diagram of a PAV vector comprising the 5' ITR and packaging sequences of Ad2 (nucleic acids 1–380) separated by a multiple cloning site into which is inserted a nucleic acid encoding αgal.

Figure 7:
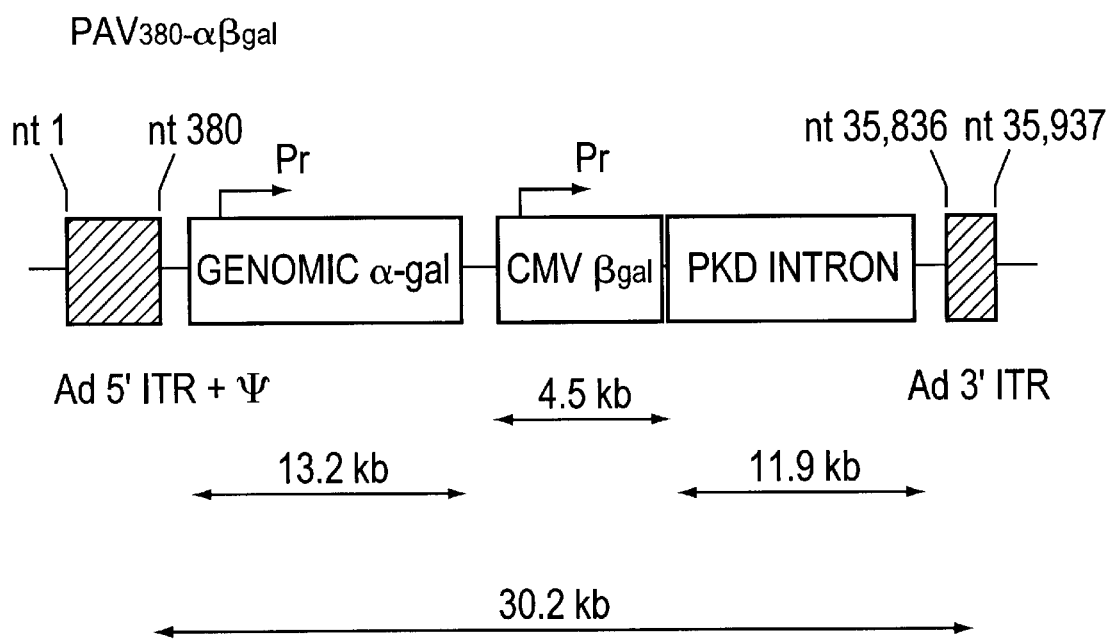

FIG. 7 shows a schematic diagram of a PAV vector comprising the 5' ITR and packaging sequences of Ad2 (nucleic acids 1–356) separated by a multiple cloning site into which is inserted a nucleic acid encoding αgal and a nucleic acid encoding βgal.

Figure 8A:
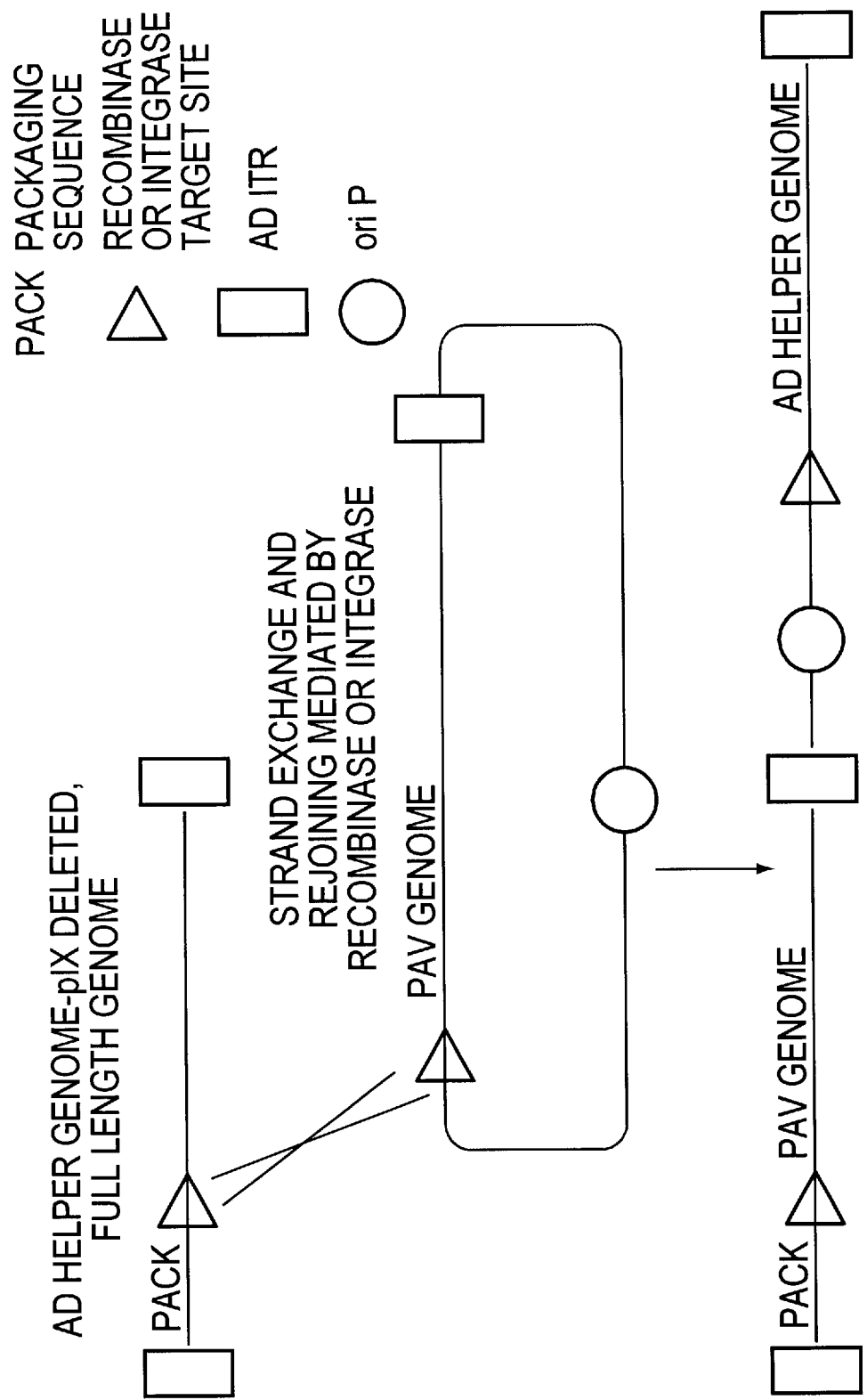
Figure 8B:
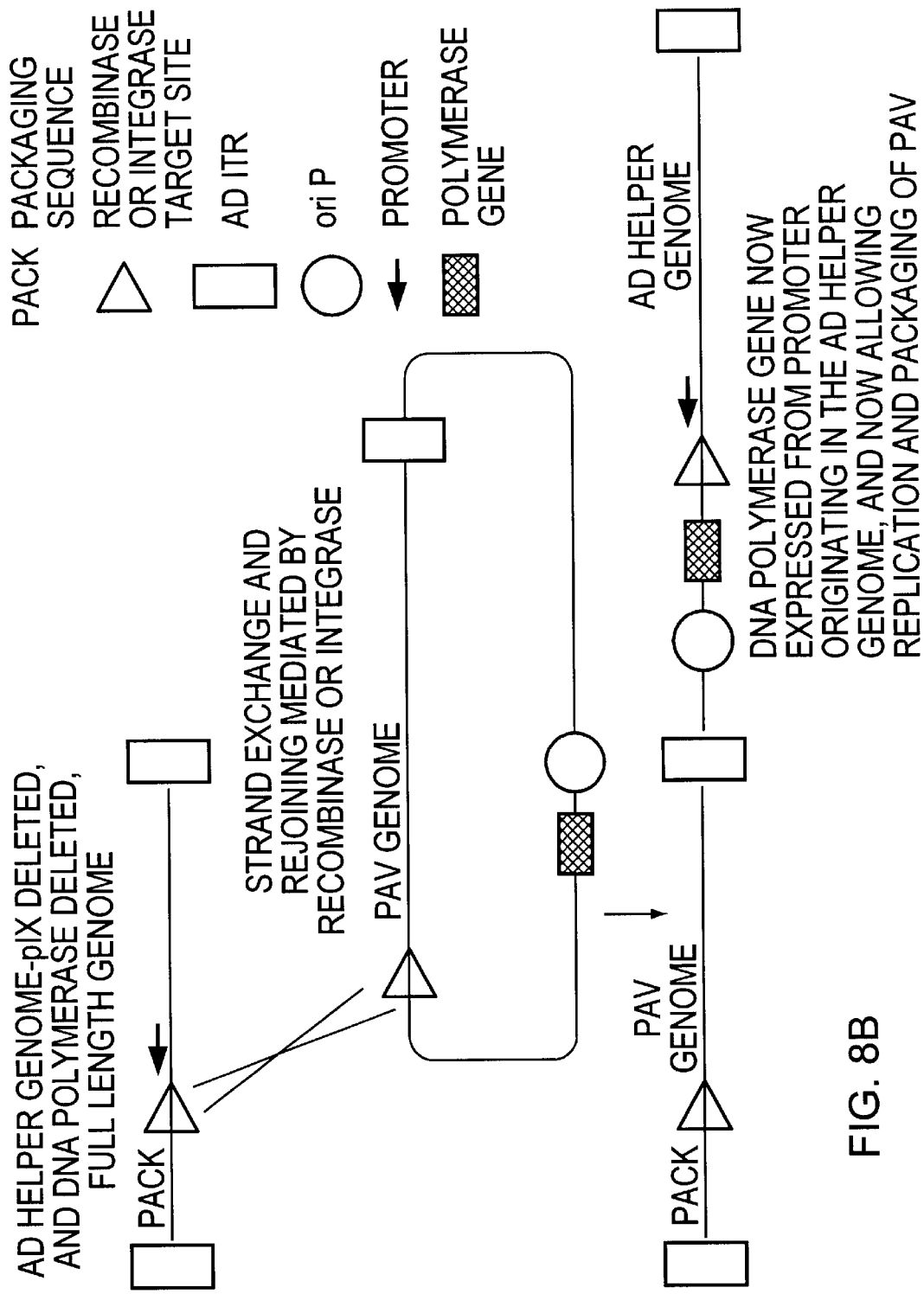

FIGS. 8A and 8B show particular embodiments of adenoviral helper genomes and PAV genomes useful in the present invention.

DETAILED DESCRIPTION OF THE INVENTION

The invention is directed to novel adenoviral helper vectors which facilitate the production and packaging of pseudoadenoviral vectors (PAV) by providing for the production of essential viral proteins in trans required for PAV production and packaging. The term PAV, as used herein, refers to adenoviral vectors derived from the genome of an adenovirus which contain minimal cis-acting nucleotide sequences required for the replication and packaging of the vector genome and which can accommodate one or more transgenes, up to about 36 Kb of foreign nucleic acid, (see, e.g., disclosure of U.S. Pat. No. 5,670,488, incorporated herein by reference). The helper vectors of the invention are packaging defective due to the inclusion of recombinase recognition sequences in their genome which function to displace the viral packaging sequences from their necessary location in proximity to the ITRs. The invention is also directed to PAV producer cell lines which are stably transfected with a PAV and which facilitate PAV production while being adaptable to large scale commercial production of PAV. The invention is further directed to a PAV shuttle vector which can be propagated in bacteria and replicated in mammalian cells lines. Such a shuttle vector is useful for in vitro applications such as for the delivery of a nucleic acid to a cell for the production of proteins in vitro and for the in vitro study of proteins in a mammalian system. The helper vectors, cell lines and PAV of the present invention are useful for the production of PAV with minimal contamination by helper vectors.

In addition to PAV, the present invention can be used with other replication incompetent adenoviral vectors. Such adenoviral vectors include partially deleted adenoviral vectors, including those described in WO99/57296, the disclosure of which is hereby incorporated herein by reference. Accordingly, wherever the term "PAV" is used in the disclosure, the skilled artisan will recognize that other replication incompetent adenoviral vectors, including partially deleted adenoviral vectors, many of which have been described in the art, may be utilized in the invention. The skilled artisan will recognize that the helper vectors, cell lines and methods of the present invention will be designed to complement the specific configuration of the adenoviral genome present in the replication incompetent adenoviral vector.

Human adenovirus genomes comprise a double-stranded linear nucleic acid of approximately 36,000 bp, with a covalently attached terminal protein (TP) at each 5' terminus. The 5' and 3' termini of adenoviruses are composed of inverted, repeated sequences ranging from 102 to 162 base pairs (Stillman, *Cell* 35:7–9, 1983). These inverted terminal repeats (ITRs) contain the origin of DNA replication and allow DNA synthesis to begin at either end of the molecule. Packaging of the linear genome occurs in a polar fashion, from left to right, due to the location of the packaging element in the left end of the molecule. The packaging element comprises a repeated motif, and it must reside near the end of the linear genome to function. For adenovirus serotype 5 (Ad5), this distance is 600 bp (Schmid and Hearing, *J. Virol.* 71:3375–3384, 1997, incorporated herein by reference). The requirement of relatively close spacing between cis elements within the ITR and packaging sequences, and the evidence for the binding of those sequences to identical cellular factors suggests a trans-acting link between Ad DNA replication and packaging. See Schmid and Hearing, *J. Virol.* 72:6339–6347, 1998, incorporated herein by reference.

A helper vector of the invention is defined as an adenovirus which is able to supply the viral proteins required in trans for the production of PAV or other minimal adenoviral vectors. In accordance with the invention, the helper vector genome is disabled for packaging, thereby allowing for preferential packaging of PAV genomes into viral particles. The helper vector genome comprises at least those genes and/or regions of the adenovirus genome that are required to produce the viral proteins required in trans for the production of PAV. The adenovirus proteins supplied by the helper vector include, inter alia, the regulatory proteins from the adenovirus early (E) genomic regions, the capsid proteins encoded by the viral late (L) genomic regions and other structural and non-structural proteins. As there may be very low levels of helper vector contamination of the final PAV preparation, it is advantageous to disable the helper vector genome by deletion of viral genes. For example, the E4 region may be deleted from the helper vector genome such that any helper vector that contaminates the final PAV preparation will be replication defective and not cause an adverse response in a subject. Similarly, the DNA polymerase gene may be deleted from the helper vector genome, such that any helper vector contamination of the final PAV preparation will also be replication defective. For full PAV replication and packaging, the genes deleted from the helper vector genome will be stably placed within the PAV producer cell, e.g., the E4 or DNA polymerase genes noted above. Helper vector genome deletions make the helper vector progressively safe and lessen the negative consequences of helper vector contamination of the final PAV preparation. The production of the proteins encoded by a helper vector genome facilitates the replication of the PAV genome during the production of PAV vector stock. The adenovirus genes required in trans are not limited by virus serotype, and the helper vectors of the invention can contain adenovirus genes from more than one serotype. Structural proteins, which are supplied by the helper vector, can therefore be chosen so that the capsid proteins are derived from a desired serotype or serotypes and optimized for a particular use. For example, adenovirus serotype 6 (Ad6) proteins may be particularly advantageous due to the fact that a majority of the population does not have high titer neutralizing antibodies to this Ad serotype.

The helper vector genome is desirably modified according to the present invention such that packaging of helper vector is impaired, or eliminated. Such disability reduces or eliminates the production of helper vector in the preparation of a PAV stock, while allowing the helper vector itself to be propagated during the separate production of a helper vector stock. A helper vector of the invention is rendered packaging-defective by incorporation into its genome, recombinase binding sequences which function to displace the packaging sequences from their necessary location in the helper vector genome in proximity to the ITRs, such displacement resulting in the inability to package. A recombinase protein which may be supplied in the producer cell lines during production of PAVs and may bind to such recombinase binding sequences inserted into the helper vector genome.

A binding protein, as referred to herein, is defined as any protein or peptide which is capable of binding to the binding sequences inserted into the genome of the helper vectors of the present invention so as to prevent packaging or any protein or peptide which is capable of binding to and inducing cleavage at a particular binding sequence. In particular, the binding protein is a recombinase which binds to specific nucleotide sequences.

The substantially helper vector-free PAV stocks of the present invention, as discussed herein, refer to PAV stocks preferably comprising less than about 5% helper vector.

Preferred specific binding sequences of the invention include, but are not limited to, those derived from (1) the FLP recombinase target site (FRT) (GAAGTTCCTATTCTCTAGAAAGTATAGGAACTTC; SEQ ID NO:1) which can catalyze site-specific excision of flanked nucleotide sequences when recognized by FLP recombinase (Senecoff et al., *Proc. Natl. Acad. Sci. USA* 82:7270–7274, 1985) and comprises a 13 base pair inverted repeat with an 8 base pair core from FRT; (2) the recognition target lox site for Cre recombinase (ATAACTTCGTATAATGTATGCTATACGAAGTTAT; SEQ ID NO:2) which can catalyze site specific excision of flanked nucleotide sequences (See Hamilton and Abremeski, *J. Mol. Biol.* 178:481–486, 1984; Hoess et al., *Proc. Natl. Acad. Sci. USA* 79:3398–3402, 1982; Parks et al., *Proc. Natl Acad. Sci. USA* 93:13565–13570, 1996) and comprise a 13 base pair inverted repeat with an 8 base pair core from loxP; and (3) the recognition site for a restriction endonuclease such as RsrII; CGGACCG (SEQ ID NO:3) or CGGTCCG (SEQ ID NO:4); the recognition target sequence for phage [φ] C31 recombinase attB GTGCCAGGGC GTGCCCT-TGG GCTCCCCGGG CGCG (SEQ ID NO:5); and attP CCCCAACTGG GGTAACCTTT GAGTTCTCTC AGT-TGGGGG (SEQ ID NO:6). Upon recognition of the FRT, Lox or phage [φ] C31 nucleotide sequences by either FRT, Lox or phage [φ] C31 recombinase, the packaging signal is displaced from its position proximal to an ITR either by a recombination event which causes the packaging signal to be moved to another location in the helper vector genome, or by a recombination event which causes the excision of the ITR sequences from the helper vector genome. Truncated and/or altered FRT, Lox or phage [φ] C31 sites which bind FRT, Lox or phage [φ] C31 respectively, are also within the scope of the present invention as well as any other sequences which facilitate the binding and recombination by FRT, Lox or phage [φ] C31 recombinase. Truncations may be made by deleting particular nucleotides and alterations may be made by mutating particular nucleotides by techniques known to those skilled in the art. Truncated and/or altered FRT, Lox or phage [φ] C31 sites may be such that binding by FRT, Lox or phage [φ] C31 recombinase is not compromised. The invention also contemplates the use of other recombinase or integrase proteins and their respective DNA sequences to which they bind. There are currently approximately 105 proteins in subgroups of site specific recombinases. See generally, Nunes-Duby et al., 1998, *Nucleic Acids Res.* 26:39–406; Argos et al., 1986, *EMBO J.* 5:433–440. In addition to Cre and FLP, a recombinase (R) encoded by the pSR1 plasmid of the yeast *Zygosaccharomyces rouxii* has similar function to FLP (Kilby et al., 1993, *TIG* 9:413–421). The "R" recombinase and its recognition sequences may also facilitate the binding and recombination referred to herein. The phage [φ] C31 recombinase system is described in Kuhstoss and Rao, *J. Mol. Biol.* 222:897–908 (1991); U.S. Pat. No. 5,190,981; Groth et al., *PNAS Early Edition*, www.pnas.org/cgi/doi/10.1073/pnas.090527097; and PCT Patent Publication WO00/11155. The disclosure of all of these publications is hereby incorporated herein by reference.

The FRT, lox, phage C31 attB, attP and other recognition and/or binding sites may be synthesized using standard techniques for oligonucleotide synthesis.

In one embodiment, the nucleotide sequences which bind a recombinase or integrase protein are placed in an inverted orientation relative to each other; the left most sequence is placed approximately between nucleotide positions 102 and 194 of the helper vector genome (FIG. 1B), and the right-most sequence is placed approximately between nucleotide positions 32,800 and 32,820 of the helper vector genome (FIG. 1B). Action of the recombinase on the cognate recombinase recognition nucleotide sequences inverts the central portion of the helper virus vector genome such that the packaging elements are displaced from their close proximity to the ITR and embedded within the right end of the helper genome at a distance of approximately 3,000 nucleotides from the ITR (FIG. 1C), a distance which significantly reduces the packaging of the helper virus vector. Such reduction of packaging of the helper virus results in the production of a PAV stock which contains less than 5% contaminating helper vector.

Figure 2B:
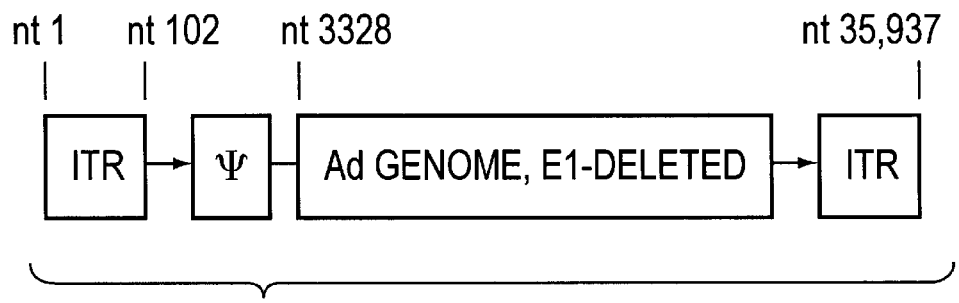
Figure 2C:
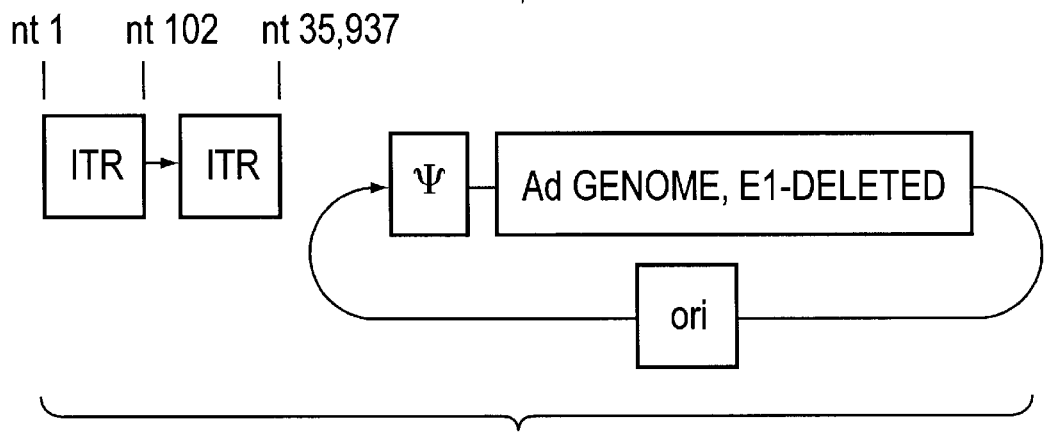

In another embodiment of the present invention, the recombinase recognition sequences are placed in the same orientation at opposite ends of the helper vector genome; the left-most sequence placed approximately between nucleotide positions 102 and 194 (FIG. 2B), and the right-most sequence placed approximately between nucleotide positions 35,614 and 35,836 (FIG. 2B). Action of the recombinase on the cognate recombinase recognition nucleotide sequences leads to formation of a circular helper genome molecule and a separate short, linear DNA that contains the left and right ITRs (FIG. 2C). The circular helper cannot be packaged because the packaging sequence is no longer adjacent, or even on the same molecule, as the ITR. Continued replication of the helper genome may be accomplished through the use of alternative replication origins, such as those derived from SV40, EBV or a eukaryotic cell, preferably mammalian cells, which are incorporated into the helper vector genome (FIG. 2C).

Standard techniques of molecular biology such as restriction enzyme digestion and ligation, polymerase chain reaction and site-directed mutagenesis can be used to create a plasmid comprising the recombinase nucleotide binding sites of the present invention. Such a plasmid can be co-transfected into a cell line with DNA encoding the remainder of the adenovirus helper genome to be contained in the helper vector, such that homologous recombination occurs, thereby generating a helper vector with the desired recombinase nucleotide binding sequence. The resultant helper vector has exposed ITRs which are available to the adenovirus DNA polymerase and terminal protein for replication of the helper vector genome. See FIG. 1B and 2B.

This allows for the propagation of the helper vector in a cell line which does not provide for the recombinase protein and therefore does not support the recombination event which renders the helper vector packaging deficient or defective (FIG. 1C and 2C). Alternatively, a single vector may be constructed which comprises the recombinase nucleotide binding sites and required sequences of the adenovirus helper genome.

Figure 4:
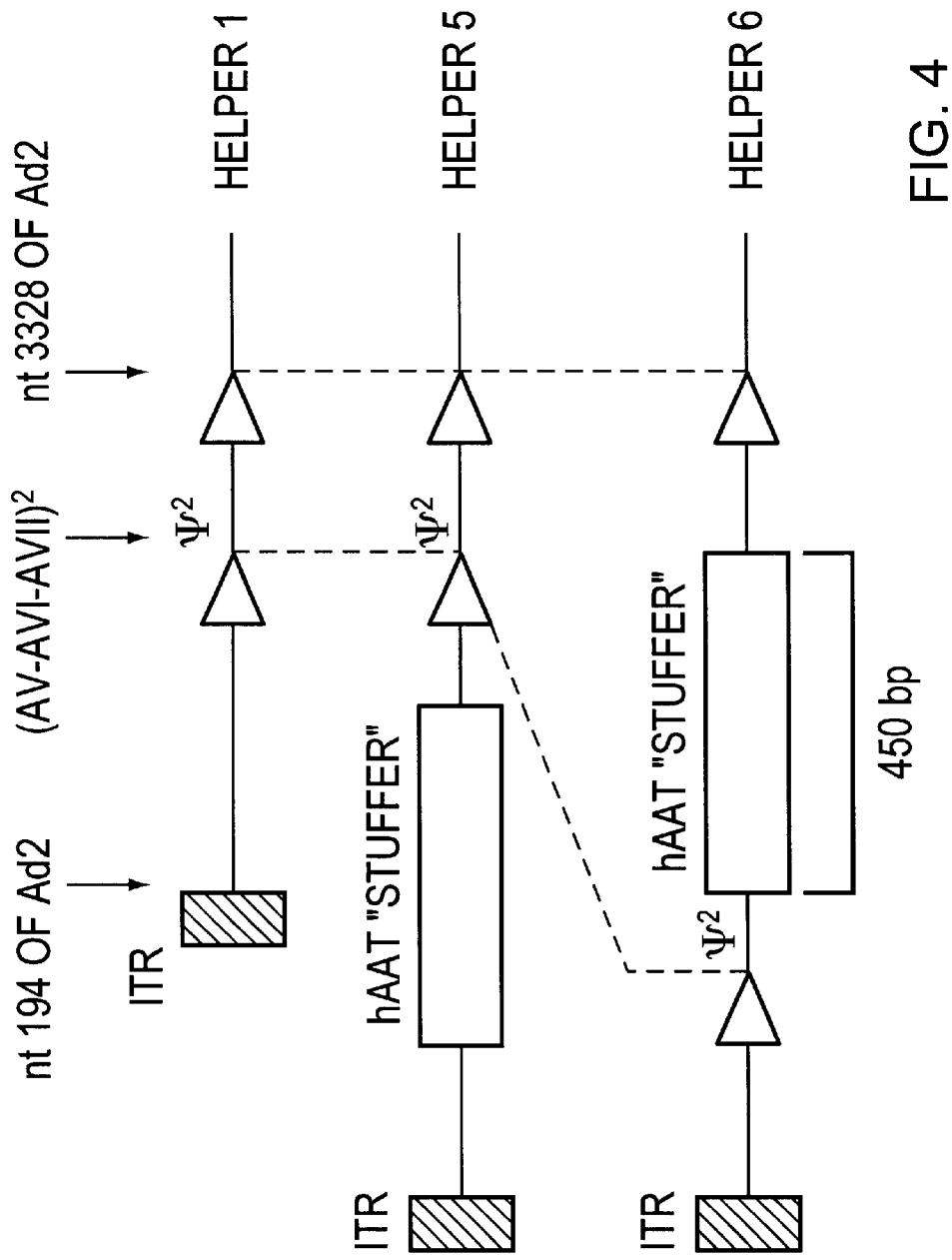
FIG. 4 shows a schematic diagram of a helper vector containing a packaging signal flanked by FRT sites and additionally containing hAAT stuffer sequences flanked by the FRT sites.

In another embodiment of the present invention, the helper vector (as depicted in FIG. 4) comprises a packaging signal region ($\Psi_2$) flanked by recombinase nucleotide binding sequences (in the figures, the symbol "→" distinguishes primers from recombinase nucleotide binding sequences; e.g. FRT), such that the binding of a recombinase at said recombinase nucleotide binding sequences excises the packaging signal region from the helper vector. The helper vector may further comprise stuffer sequences which may improve excision of the packaging elements. The packaging signal region generally contains a minimum of seven AT-rich elements, denoted AI–AVII. These seven AT-rich elements are located in the adenovirus genome from nucleotides 194–380 (referencing adenovirus serotype 5, Schmid et al., *J. Virol.* 71:3375–84, 1997). The helper virus genome may be modified by the deletion of packaging elements AI through AIV, retaining only the packaging elements AV, AVI, and AVII or a repeated (AV-AVI-AVII)$_2$ motif (FIG. 4). Recombinase nucleotide binding sequences, such as FRT or attB and attP sequences, may flank the packaging elements (FIG. 4; Helper 1). In addition, hAAT stuffer sequences may be placed either 3' or 5' to the packaging elements and between the recombinase nucleotide binding sequences (FIG. 4; Helper 5 and Helper 6). A stuffer sequence is a term generally recognized in the art intended to define functionally inert nucleotide sequence. The stuffer sequence may be a nucleotide sequence which does not code for a protein and may be derived from intron sequences or other noncoding nucleotide sequences (e.g. a 450 bp DNA derived from intron sequences from human α-antitrypsin (hAAT); see FIG. 4). The stuffer sequences are useful to improve excision of the packaging elements from the helper vectors of the present invention. Contaminating helper vector may be eliminated or greatly reduced in PAV stocks by techniques known in the art.

When the helper vector is supplied to a cell line, e.g. 293 cells (Graham et al., *J. Gen. Virol.* 39:59–72, 1977), along with a packaging deficient PAV and a source for the recombinase protein (e.g. the cell line may produce the recombinase protein, a vector may additionally be supplied encoding for the recombinase protein, the PAV may encode for the recombinase protein, or the helper vector itself may have an inducible promoter driving the expression of the recombinase protein such that the recombinase would only be expressed during PAV production), PAV can be replicated and packaged by the necessary proteins provided in trans by the helper vector, while the helper vector itself cannot be packaged due to the rearrangement or excision of the ITR sequences such that packaging cannot proceed. The PAV and the helper vector can contain signal regions or ITR sequences from different adenovirus serotypes such that sequence overlap between the PAV and the helper vector is minimized and the possibility of recombination is reduced.

Figure 3:
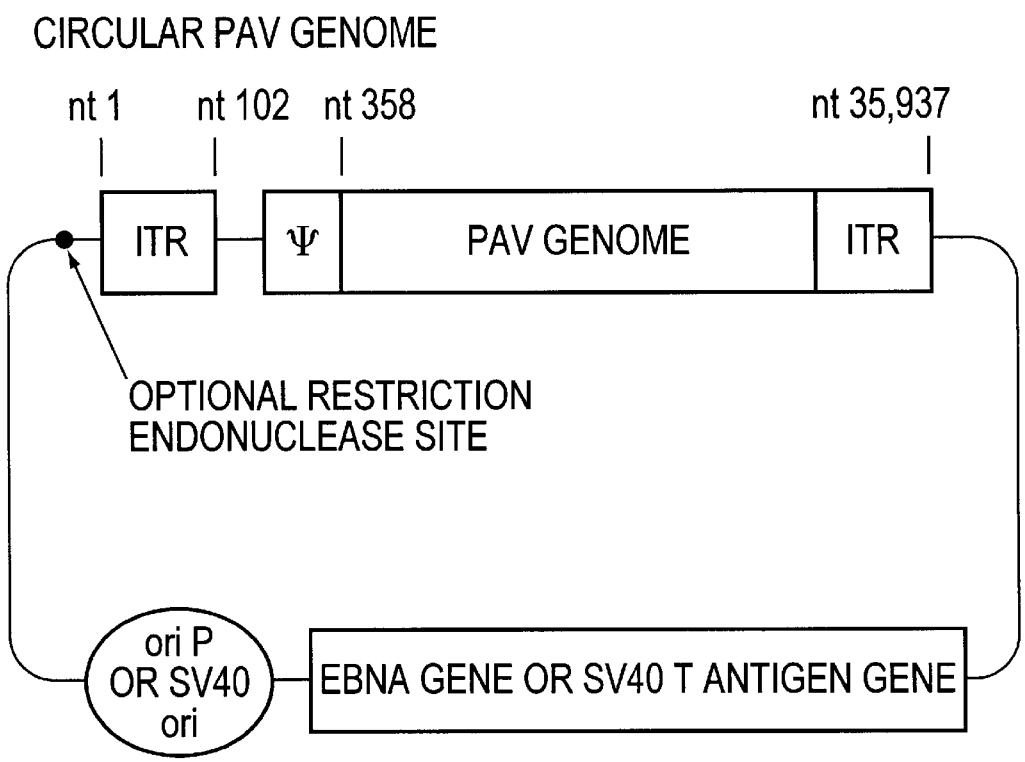
FIG. 3 shows a schematic diagram of a circular pseudoadenoviral (PAV) vector comprising a bacterial plasmid genome for propagation of the PAV in bacteria and replication sequences from the EBV genome for replication in mammalian cell lines.

The invention is further directed to PAV shuttle vectors comprising a bacterial plasmid genome, e.g. pBR322, or a bacterial origin of replication and drug selection sequences and a mammalian replication origin, such as replication origin sequences from the EBV genome or the SV40 genome (see FIG. 3). The bacterial plasmid genome or bacterial replication origin and drug selection sequences allows for the production of the PAV in bacteria and the mammalian origin of replication allows for the replication of the PAV in mammalian cells. Additionally, the PAV vector may comprise a transgene and a nucleic acid encoding EBNA or SV40 large T antigen, alternatively, the nucleic acid encoding the EBNA or SV40 large T antigen may be placed within the genome of the mammalian producer cell line or on a separate plasmid. The PAV is circular (FIG. 3), making the ITRs embedded rather than free, thereby reducing the efficiency of replication and packaging of the PAV, as compared to a PAV with free ITRs. However, once one of the ITRs becomes available, a process that is known to occur (Graham, 1984, *EMBO* 3:2917–2922; Matani et al, 1995, *Proc. Natl. Acad. Sci. USA* 92:3854–3858; Hardy et al., 1997, *J. Virol.* 71:1842–1849; Fisher et al., 1996, *Virol.* 217:11–22), then replication and packaging of the PAV vectors will proceed efficiently. Alternatively, the PAV ITRs may be flanked by a restriction endonuclease nucleotide binding site which, when cleaved by a restriction enzyme, e.g. RsrII, free the ITRs to promote efficiency of replication and packaging of the PAV. Generally, the PAV vectors of the present invention comprise two ITR sequences and the minimal adenovirus 5' sequences required for helper vector-dependant replication and packaging of the PAV. See U.S. Pat. No. 5,882,877, incorporated herein by reference. The PAVs of the present invention contain no potentially harmful viral genes, have a capacity for foreign nucleic acids of approximately 36 kb, may be produced in reasonably high titers and maintain the tropism of the parent virus for dividing and non-dividing target cell types. See U.S. Pat. No. 5,882,877.

The invention is also directed to methods for the production of PAVs and other deleted adenoviral vectors in high yield, using the helper vectors, PAVs and producer cell lines of the present invention. In such methods, PAV is preferentially produced, generating an enriched preparation which is substantially free of contaminating helper vector. To produce a PAV vector stock, the PAV genome, which comprises the adenovirus 5' ITR and packaging signal and 3' ITR, and further comprises one or more transgenes up to 36 kb in size, operably linked to expression control sequences, can be engineered as a circular PAV and can be stably introduced into a cell to provide an improved cell line for the production of PAV. PAV can be delivered to cells by any method of nucleic acid transfer, including, but not limited to, transfection, lipofection and electroporation to produce the PAV-transfected cells of the invention. As stated above, helper vector can be provided to the PAV-transfected cell line to initiate PAV production thus eliminating the need for multiple rounds of infection and reducing the time and effort required to produce a PAV stock. In a preferred embodiment of the invention, 2 to 20 µg of PAV DNA is delivered to a cell by lipofection using lipofectamine (Gibco BRL, Rockville, Md.) or a CaPO$_4$ kit such as Profectin (Promega, Madison, Wis.), and the cells are infected with a helper vector of the invention using a multiplicity of infection (MOI) of 0.5 to 10.

The improved helper vectors comprise recombinase nucleotide binding sites which either excise or rearrange the ITR sequences of the helper vector to reduce or eliminate helper vector contamination of the PAV stock. The reduction or elimination of helper vector contamination eliminates or reduces the need for purification procedures to remove contaminating helper vector. Additionally, the improved cell lines and helper vectors are amenable to adaptation to large scale commercial production due to the simplification and elimination of the need for lengthy production and purification protocols.

In a particular preferred embodiment of the present invention, the helper vectors comprise phage [φ] C31 nucleotide binding sites attB and attP located such that they will either excise, rearrange or otherwise deactivate the ITR sequences of the helper vector to reduce or eliminate helper vector contamination of the PAV stock, for example by preventing packaging from occurring. The phage [φ] C31 recombinase offers particular advantages for the methods of the present invention in that the excision reaction is essentially a one way reaction; very little, if any, of the reverse process [integration] will occur. Thus, the reappearance of helper vector which can be packaged and produce contaminating helper virus is minimized. This is particularly critical for the improved safety and efficacy of production of recombinant adenoviral stocks for use in gene therapy. The phage [φ] C31 sequences minimally required for use as recognition sites have recently been identified, the length of these sequences, attB and attP, being approximately 34 and 39 nucleotides, respectively [Groth et al., *PNAS Early Edition*, supra]. In the present invention, we have shown that the phage [φ] C31 recombinase system may be used in practical applications to viral vector production, as described herein. Thus, in the preferred embodiment of the present invention phage C31 recognition sites are employed.

If purification of the PAV is desired or required, purification of the PAV from the cell line of the invention can be performed by standard techniques of virus purification known to those skilled in the art. For example, viruses in cell lysates from producer cells can be purified on standard CsCl gradients. The PAV particles are of lower density relative to the helper particles and will band at a higher position in the gradient, allowing for direct isolation and recovery. Alternatively PAV purification can be performed using chromatographic techniques, e.g., as set forth in Published PCT Application WO 97/08298, incorporated herein by reference.

PAV yield is calculated by measuring the DNA and protein composition of the purified preparation. Maizel et al. (*Virology* 36:115–125, 1968) determined that an adenovirus virion comprises 13% DNA, with the remainder being protein.

Preferred transgenes for use in the methods of the present invention include hemophilic factors, preferably Factor VIIa [U.S. Pat. No. 4,784,950]; Factor VIII [U.S. Pat. Nos. 4,965,199; 4,868,112 [B-domain deleted] and and U.S. Pat. No. 5,661,008]; and Factor IX [U.S. Pat. No. 4,994,371]. Other preferred transgenes are those which encode lysosomal storage enzymes, including genes encoding glucocerebrosidase [Gaucher's disease; U.S. Pat. Nos. 5,879,680; 5,236,838]; alpha-galactosidase [Fabry Disease; U.S. Pat. No. 5,401,650]; acid alpha-glucosidase [Pompe's Disease; WO00/12740]; alpha-n-acetylgalactosaminidase [Schindler Disease; U.S. Pat. No. 5,382,524]; acid sphingomyelinase [Niemann-Pick disease; U.S. Pat. No. 5,686,240]; alpha-iduronidase [WO9310244A1]. Other preferred transgenes include the genes for CFTR, dystrophin and alpha-antitrypsin.

Transgene activity of a PAV preparation may be monitored by immunoflourescent techniques by infecting 293 cells with the PAV, then using an antibody against a PAV-encoded transgene expression product (protein) to determine infectious particles. Alternatively, the activity of an enzyme encoded by a transgene can be measured (e.g. β-galactosidase, α-galactosidaseA, α-antitrypsin), by, for example, an ELISA assay. Where the transgene is CFTR, expression of a CFTR transgene in target cells from a subject with cystic fibrosis is correlated with production of a functional chloride ion channel in such cells that may be measured by techniques known in the art. Likewise, where the transgene is α-galactosidase, its expression in target cells from an individual with Fabry's disease (α-galactosidase minus) can be monitored by a decrease in stored lipid substrate, GL3, see, e.g., PCT/US98/22886, filed 10.29.98, incorporated herein by reference.

The ability of PAV to enter cells may be determined by measuring the amount of viral capsids that bind to the cells with anti-adenovirus antibodies. Demonstration of the entry of the PAV genome into a cell can be performed by flourescent in situ hybridization (FISH).

Minimal contamination of the PAV stock is expected using the novel helper viruses of the invention. Helper virus production, if any, can be scored, for example, by standard plaque assays on 293 cells. Preferably, the ratio of PAV to helper vector will be greater than 10,000 to 1.

The practice of the invention employs, unless otherwise indicated, conventional techniques of protein chemistry, molecular virology, microbiology, recombinant DNA technology, and pharmacology, which are within the skill of the art. Such techniques are explained fully in the literature. See, e.g., *Current Protocols in Molecular Biology*, Asubel et al., eds., John Wily & Sons, Inc., New York, 1995, and Remington's Pharmaceutical Sciences, 17th ed., Mack Publishing Co., Easton, Pa., 1985.

The invention is further illustrated by reference to the following examples.

EXAMPLES

Example 1

Establishing a Cell Line Expressing Flp Recombinase

An essential component of the PAV and PAV helper systems described herein is a cell line that expresses a recombinase protein. Flp is a recombinase derived from yeast with an optimal reaction temperature of 30° C. (Buchholz et al., 1998, *Nature Biotechnol.* 16:657–662). To make this enzyme more useful when expressed in mammalian cells, a thermal resistant form of the enzyme has been engineered (Buchholz et al., 1996, *NAR* 24:4256–4262); this thermal resistant form of Flp is known as Flpe6. Mammalian cells in which the action of this enzyme is used for PAV packaging include 293 cells (Graham, F. L., J. Gen. Virol. 36:59–72, 1977), PERC6 (Fallaux et al., *Human Gene Therapy* 9:1909–17(1998)) cells, HeLa cells (ATCC, Bethesda, Md.), A549 cells (Imler et al., Gene Therapy 3:75–84, 1996), as well as variants of these cells that have been altered by the introduction of the tetracycline gene expression control system (Gossen and Bujard, 1992, *Proc. Natl. Acad. Sci. USA* 89:5547; Gossen et al., 1995, *Science* 268:1766). Expression of the Flpe6 enzyme is achieved by cloning the Flpe6 coding sequence into the expression cassette within the plasmid pCEP4 (Invitrogen, Carlsbad, Calif.) which contains the CMV promoter and the gene encoding hygromycin drug resistance. An alternate expression system for Flpe6 is obtained by cloning the Flpe6 coding sequence into the expression cassette in the plasmid pTRE which contains a minimal promoter regulated by the tetracycline gene control system. Gossen and Bujard, *Proc. Nail. Acad. Sci.* USA 89:5547–5551, 1992; and Gossen et al., Science 268:1766–1769, 1995, both incorporated here by reference, have designed a system wherein gene expression from a minimal promoter is under strict control of the tetracycline repressor (TetR), expressed as a fusion protein with the herpes virus VP16 transcriptional activation domain (VP16). Two versions of the TetR/VP16 protein exist: the wild type TetR is active only in the absence of tetracycline or doxycycline, while a mutated form of TetR (reverse TetR or rTetR) is active only in the presence of doxycycline. When linked to VP16, the TetR form activates transcription only in the absence of tetracycline and the rTetR form activates transcription only in the presence of doxycycline. Each of these transcriptional control factors, TetR/VP16 and rTetR/vp16 controls the expression of genes linked to a minimal promoter cloned adjacent to tetracycline transcriptional regulatory elements (TRE). In Tet-off cells, the presence of tetracycline in the cell culture medium prevents expression of Flpe6 by binding to the TetR/VP16 fusion protein. When tetracycline is removed from the cell culture medium, repression is relieved and expression of Flpe6 occurs.

A. PERC6/Flpe6 Cell Line

PERC6 cells (Fallaux et al., *Human Gene Therapy* 9:1909–17 (1998)) were plated at $7.8 \times 10^6$ cells/10 cm dish and transfected with 10 μg of pCEP-4/Flpe6 plasmid using 60 μl of lipofectamine. Three days post transfection, plates were split to 15 cm plates and drug selection was applied (150 μg/ml hygromycin). Media was changed 2–3 times per week until colonies were picked 3 weeks post transfection. Cell clones were then put under maintenance dosage of hygromycin (100 μg/ml).

B. 293 tet-off/Flpe6 Cell Line

293 Tet-Off cells were seeded into Biocoat Collagen I 10 $cm^2$ dishes (Becton Dickinson, Bedford, Mass.) at $6 \times 10^5$ cells per dish the day before transfection. The next day, medium was removed from the plates and replaced with ~10 ml of fresh medium three hours prior to time of transfection. Approximately 45 minutes before transfection, a Calcium Phosphate transfection mixture was prepared using the desired plasmid DNA according to the Promega Profectin Mammalian transfection protocol. Cells were transfected with 10 μg of pTRE/Flpe6 DNA and 2 μg of pTK Hygromycin resistance marker DNA. The transfection mixture was allowed to precipitate for half an hour before being added drop-wise to cells on plates. The next day, the plates were washed with fresh medium and re-fed. Two days later, the plates were harvested and plated out to 150 mm dishes. Twelve plates were seeded at 2000–2500 cells per plate. The DNA cloning plates receive -MEM medium containing 15% Tet System Approved FBS, 2 μg/ml of Tetracycline, 2 mM L-Glutamine, 100 μg/ml of G418, and 50 μg/ml of Hygromycin for selection. Plates were incubated for a two week period, and were inspected for colonies of drug resistant cells. Hygromycin resistant clones which were isolated using 8 cm cloning rings and silicon grease.

Example 2

Improved Helper Vector Where the Packaging is Impaired Due to Repositioning of the Packaging Sequence to an Internal Position in the Helper Genome In this helper construct, the nucleotide sequences which bind the Flp recombinase protein are placed in an inverted orientation relative to each other. The recognition sequence for the Flp recombinase is referred to as FRT and has the following sequence: GAAGTTCCTATTCTCTAGAAAG-TATAGGAACTTC (SEQ ID NO:1). The left most FRT sequence is placed such that it follows nucleotide position 102 of the helper vector genome (FIG. 1B), and right-most FRT sequence is placed such that it follows nucleotide positions 32,820. (FIG. 1B). When this helper vector genome is introduced into the Flp-expressing producer cell, action of the Flp recombinase on these FRT sequences inverts the central portion of the helper vector genome such that the packaging elements are displaced from their close proximity to the ITR and embedded within the helper genome at a distance of approximately 3,000 nucleotides from the ITR (FIG. 1C), a distance which reduces the packaging of the helper virus vector such that there is less than 5% contamination of the PAV preparation by the helper vector.

The FRT sequences are prepared as synthetic oligonucleotides and are inserted into the desired positions within the helper genome using standard molecular cloning methods. The helper vector genome, cloned as a plasmid bearing the entire helper genome (Souza and Armentano, 1999, *Biotechniques* 26:502–508), is converted to an infectious virus by transfection into 293 cells or PERC6 cells (0.5 to 10 micrograms of DNA) using standard calcium phosphate or lipofectamine. Alternatively, the helper virus genome is cloned into two or more DNA fragments, each with overlapping segments of the helper genome such that recombination between the separate helper DNA fragments occurs after transfection into 293 or PERC6 cells, resulting in the generation of infectious helper virus. Evidence of viral infection is noted by generalized cytopathic effect or the presence of distinct viral plaques. The helper virus is recovered by passaging on 293 cells to provide a helper virus stock.

Example 3
Improved Helper Vector Where the Helper Vector is Converted to an Episomal Form Lacking ITRs During PAV Production In this helper construct, the nucleotide sequences which bind the Flp recombinase protein are placed in the same orientation relative to each other. The recognition sequence for the Flp recombinase is referred to as FRT and has the following sequence: GAAGTTCCTATTCTCTAGAAAG-TATAGGAACTTC (SEQ ID NO:1). The left most sequence is placed such that the 5' G nucleotide of the FRT sequence follows nucleotide position 102 of the helper vector genome (FIG. 1B), and the 5' G of the FRT sequence follows nucleotide positions 35,835 in one helper version, following nucleotide position 35,850 in a second helper version, and following nucleotide position 35,875 in a third helper version. (FIG. 1B). When any of these helper genomes containing FRT sequences is introduced into the Flp-expressing producer cell, action of the Flp recombinase on the FRT sequences converts the linear helper genome to a circular episomal form which now lacks the ITRs. Because the packaging sequence is now separated from the ITRs, the helper genome cannot be packaged. Additionally, the fact that the packaging sequence in buried within the helper genome further prevents packaging. The helper with this arrangement of FRT sequences yields less than 5% contamination of a PAV stock preparation by the helper vector.

Replication of the episomal helper genome is driven by the inclusion of oriP sequences from the EBV genome. These sequences are isolated from the plasmid pCEP-4 (Invitrogen) by PCR or enzyme digestion and are inserted into the helper genome at nucleotide position (27,973–30,937 to replace the E3 region; Δ2.9). Replication from oriP is driven by the action of the EBNA gene from EBV. The gene for EBNA is included in the plasmid pCEP-4 (Invitrogen), and in introduced into the cell by standard transfection methods.

The FRT sequences are prepared as synthetic oligonucleotides and are inserted into the desired positions within the helper genome using standard molecular cloning methods. The helper genome cloned as a plasmid bearing the entire helper genome (Souza & Armentano 1999, *BioTechniques*, 26, 502–508)) is converted to an infectious virus by transfection into 293 cells or PERC6 cells (0.5 to 10 micrograms of DNA) using standard calcium phosphate or lipofectamine. Alternatively, the helper virus genome is cloned into two or more DNA fragments, each with overlapping segments of the helper genome such that recombination between the separate helper DNA fragments occurs after transfection into 293 or PERC6 cells, resulting in the generation of infectious helper virus. Evidence of viral infection is noted by generalized cytopathic effect or the presence of distinct viral plaques. The helper virus is recovered by passaging on 293 cells to provide a helper virus stock.

Example 4
Cell Line Bearing an Episomal PAV Genome

Mammalian cells appropriate for bearing episomal PAV genomes include 293 cells, PERC6 cells, HeLa cells, A549 cells, as well as variants of these cells that have been altered by the introduction of the tetracycline gene expression control system (Gossen and Bujard, 1992, *Proc. Natl. Acad. Sci. USA* 89:5547; Gossen et al., 1995, *Science* 268:1766). Flpe6 sequences are incorporated into the cells as described above. Circular bacterial plasmids containing an entire Ad genome, their construction, and manipulation have been described (Souza and Armentano, 1999, *Biotechniques* 26:502–508). In the current example, the Ad sequences that are retained are those required for PAV (U.S. Pat. No. 5,882,877, issued Mar. 16, 1999, incorporated herein by reference), the ITR sequences and packaging sequences. The remainder of the PAV genome comprises the transgene of interest and stuffer sequences as may be required. (e.g. PAV356-αgal, PAV380-αgal, PAV380-αal FIGS. 5, 6 and 7 respectively). Within the bacterial plasmid region of this construct, the oriP and EBNA genes from EBV are cloned as well as the drug resistance gene (e.g., hygromycin, G418, blasticidin) to provide a means of maintaining the episomal PAV within the cell. A variant of the episomal PAV genome is constructed where an additional ITR is placed directly adjacent to the left ITR in a head to tail fashion.

Excision of the left end of the PAV genome occurs when the cell is infected with a PAV helper, and packaging of the PAV into virions ensues. The rate of excision is increased from the head to tail left-hand ITR configuration of episomal PAV. Excision of the left end of the PAV episome is also enhanced by incorporating recognition sequences for restriction endonucleases at positions immediately flanking the outer limits of the ITRs. Appropriate restriction endonucleases for this purpose include RsrII, I-CeuI, I-PpoI, and others for which there are no recognition sequences within the helper genome or the PAV genome. The expression cassettes encoding the cognate restriction endonuclease are incorporated into the helper Ad genome such that, upon infection of the PAV episome bearing cell, the endonuclease is expressed and liberates the left end of the PAV episome.

Example 5
Phi C31 Subcloning and Expression Plasmids

The Phi C31 integrase cDNA was PCR amplified from phi C31 DNA (gift Keith Chater, John Innes Center, England) in a 50 uL reaction volume containing IX Pfu buffer (Stratagene, La Jolla, Calif.), 100 ng forward primer phi-1 (5'-ACC GCT CGA GAT GAC ACA AGG GGT TGT GAC C)[SEQ ID NO:7] and 100 ng reverse primer phi-2 (5'-GTC GAC TAG TCT ACG CCG CTA CGT CTT CCG T)[SEQ ID NO:8] and 5 units of Pfu polymerase. The reaction was subjected to 35 cycles at 94° C. for 1 minute, 55° C. for 1 minute, and 72° C. for 2 minutes. The 1843 bp product was subcloned into the Xho I and Spe I site of vector pCMV to create pCMVint and completely sequenced.

A previral target plasmid containing two copies of Ad2 packaging elements (AV-AVI-AVII) flanked by attP and attB attachment sites was constructed by annealing oligos att-1 (5'-CTA GTC CCC AAC TGG GGT AAC CTT TGA GTT CTC TCA GTT GGG GGC GCG TAA TAT TTG TCT AGG GCC GCG GGG ACT TTG ACC GTT TAC GTG GAG ACT CGC G) [SEQ ID NO:9], att-2 (5'-CTC CAC GTA AAC GGT CAA AGT CCC CGC GGC CCT AGA CAA ATA TTA CGC GCC CCC AAC TGA GAG AAC TCA AAG GTT ACC CCA GTT GGG GA)[SEQ ID NO:10], att-3 (5'-TAA TAT TTG TCT AGG GCC GCG GGG ACT TTG ACC GTT TAC GTG GAG ACT GCT AGC GTG CCA GGG CGT GCC CTT GGG CTC CCC GGG CGC GAC GCG)[SEQ ID NO:11], and att-4 (5'-CGC GTC GCG CCC GGG GAG CCC AAG GGC ACG CCC TGG CAC GCT AGC AGT CTC CAC GTA AAC GGT CAA AGT CCC CGC GGC CCT AGA CAA ATA TTA CGC GAG T)[SEQ ID NO:12] and subcloned into the Spe I and Mlu I site of an Ad2 packaging deleted plasmid to create pAd/att. pAd/att contains Ad2 nucleotides 1–194 and 3328–10685.

In vitro Transcription and Translation

In vitro transcription and translation reactions were performed using the TnT Coupled Reticuloyte Lysate System (Promega, Madison, Wis.). Briefly, 1 μg of pCMVint plasmid DNA was mix with TnT Lysate Reaction components in the presense of $^{35}$S-methionine according to the manufacturer's instructions. Reactions were incubated for 2 hr at 37° C. and stopped by adding 0.1 volumes SDS sample buffer. Five microliters was heat denatured at 95° C. for 2 minutes and electrophoresed through a 4–15% SDS PAGE gel (Bio-Rad, Hercules, Calif.) for 1 hr at 125 volts. The gel was dried under vaccuum at 80° C. and exposed to autoradiography film for 1 hr. A band of ~85 kd corresponding to the phi C31 integrase was present.

Integration assay

To test for integration, 5 μg of pAd/att (target plasmid) and 5 μg of pCMVint (assay plasmid) were cotransfected into subconfluent 293 cells by the calcium phosphate coprecipitation method. The following day, cells were fed with fresh media supplemented with 50 μg/mL DNase I to remove residual plasmid DNA. Total DNA was isolated 48 hr post transfection and ¹⁄₄₀ of the material was subjected to PCR using primers flanking the attP and attB sites. PCR was performed using 5 μL DNA as template, 100 ng forward primer 2900LC (5'-GTG ACG TAG TAG TGT GGC)[SEQ ID NO:13], 100 ng reverse primer 2876LC (5'-ACA CTA CGA CCT ACA CTG G)[SEQ ID NO:14], 1X Taq polymerase buffer (Promega, Madison, Wis.), 200 nM each dNTP, and 5 units Taq polymerase (Promega). Reactions were cycled 35 times at 94° C. for 1 minute, 55° C. for 1 minute, and 72° C. for 2 minutes. Products were separated on a 2% super fine resolution agarose gel (Amresco, Solon, Ohio). Expected sizes are 399 bp for unintegrated products which retain the Ad2 packaging sequence and ~270 bp for products deleted of the packaging sequence by integration between attP and attB sites.

Phage C31 Recognition Site-Containing Helper Adenovirus

In a particular embodiment of the invention, a partially deleted adenoviral helper virus is employed in which the adenoviral protein IX relocated and most of the E4 region deleted, except for retaining the E4ORF6 region. Such adenoviral vectors are described, for example, at U.S. Pat. No. 6,093,567, the disclosure of which is hereby incorporated herein by reference. The packaging signal of the helper virus is flanked by attB and attP recognition sites to allow for disabling packaging of the helper virus.

Phage C31 Integrase-Containing Vectors and Cell Lines

The packaging cell line for the adenovirus is transfected with a phage C31 integrase plasmid or virus comprising a promoter operably linked to a DNA coding sequence encoding the phage c31 integrase, and an operably linked polyadenylation [PA] sequence. The phage C31 integrase plasmid may be stably incorporated into a cell line, such as a 293-based cell line or PERC6. The promoter is preferably a constitutive promoter which is well-expressed in the packaging cell, such as the cytomegalovirus promoter [CMV], or an inducible promoter such as the ecdysone promoter. The polyadenylation sequence may be any appropriate PA sequence, such as the SV40 PA.

Example 6

Experiment with Increasing Helper Contamination Upon Passaging

Several PAV amplifications with performed using three different helpers. In amplification #M2, we used H16 cells and the Ad2Ψ2hAAT helper as follows: H16 cells were plated at 1E6 cells/6 cm plate and calcium phosphate transfected with a co-precipitate containing 12 μg PAV$_{380}$αβ-gal (RsrII linearized) and Ad2Ψ2hAAT helper (moi=25). Lysate harvested 3 days post transfection had a helper titer of 9E5 IU/ml by hexon staining. Four mls of this lysate was used to infect cells plated at 1E6cells/6 cm plate. Lysate harvested 7 days post infection had a helper titer of 6.4E5 by hexon staining. Four mls of this lysate was used to infect 1E6 cells/6 cm plate. Lysate harvested 5 days post infection had a helper titer of 1.3E7 IU/ml by EGFP staining. 2.5 mls of this lysate was used to infect 1E6 cells/6 cm plate. Lysate harvested 2 days post infection had a helper titer <1.4E7 IU/ml by hexon staining. 3.5 mls of this lysate was used to infect 3E6 cells/10 cm plate. Lysate harvested 4 days post infection had a helper titer of 3.4E7 by hexon staining. 8.5 mls of this lysate was used to infect 1E7cell/15 cm plate. The harvested lysate had a titer of 4E7

Isolation of Helper Vectors that had Mutations in the FRT Sites

Lysate from amplifications was used to infect H16 cells at an MOI of 5. Hirt DNA was isolated. PCR was done on the Hirt DNA using primers flanking the FRT sites. The PCR products corresponding to the unflipped product were cloned into the pCR2.1-TOPO vector and sequenced.

Preparation of Hirt DNA

Cells were lysed in 10 mM Tris, 10 mM EDTA and 0.6%SDS. Following the addition of 1M NaCl, the lysate was pronase-treated and cleaned up by phenol/chloroform.

The invention described and claimed herein is not to be limited in scope by the specific embodiments and examples herein disclosed; these embodiments are merely intended as illustrations of several aspects of the invention. Numerous equivalent embodiments are intended to fall within the scope of this invention. Indeed, various modifications of the invention in addition to those shown and described herein will become apparent to those skilled in the art from the foregoing description. Such modifications are also intended to fall within the scope of the appended claims. The disclosure of all publications referred to herein are hereby incorporated by reference.

We claim:

1. An adenoviral helper vector consisting essentially of (1) an adenovirus genome encoding replication proteins, structural proteins, packaging elements and adenovirus ITR sequences required for the packaging of adenoviral vector particles and (2) a phage C31 recombinase nucleotide recognition sequence selected from the group consisting of SEQ ID NO: 5 or SEQ ID NO: 6, which is inserted into said genome in a location thereof to allow for the translocation or excision of said ITR sequences.

2. The adenoviral helper vector of claim 1 further comprising a eukaryotic origin of replication.

3. The adenoviral helper vector of claim 2 wherein the eukaryotic origin of replication is selected from the group consisting of the SV40 origin of replication, the EBV origin of replication and an origin of replication derived from a eukaryotic cell, preferably a mammalian cell.

4. The adenoviral helper vector of claim 1 wherein two phage C31 recombinase nucleotide recognition sequences selected from the group consisting of SEQ ID NO: 5 or SEQ ID NO: 6, which is inserted into said genome in an inverted orientation relative to each other, such that action of a recombinase upon said recognition sequences displaces said ITR sequences from the packaging elements whereby said helper vector is rendered packaging defective.

5. The adenoviral helper vector of claim 1 wherein two phage C31 recombinase recognition sequences selected from the group consisting of SEQ ID NO: 5 or SEQ ID NO: 6, which is inserted into the adenovirus genome in the same orientation relative to each other such that action of a recombinase upon said recognition sequences results in the excision of ITR sequences, whereby said helper vector is rendered packaging defective.

6. The adenoviral helper vector of claim 1 wherein two phage C31 recombinase nucleotide recognition sequences are inserted into said genome in the same orientation relative to each other, and at opposite ends of the helper genome, such that action of the recombinase on the phage C31 recombinase recognition sequences leads to formation of a circular helper genome molecule and the ITRs are excised entirely out of the genome, whereby the helper genome cannot be packaged because the packaging sequences are no longer adjacent to an ITR.

7. The adenoviral helper of claim 1 wherein the structural proteins are derived from adenovirus serotype 6(Ad6).

* * * * *